US006579857B1

(12) United States Patent
Lind et al.

(10) Patent No.: US 6,579,857 B1
(45) Date of Patent: Jun. 17, 2003

(54) COMBINATION CANCER THERAPY COMPRISING ADENOSINE AND DEAMINASE ENZYME INHIBITORS

(75) Inventors: Stuart E. Lind, Winnetka, IL (US); Catherine P. Barry, Deerfield, IL (US)

(73) Assignee: Evanston Northwestern Healthcare Research Institute, Evanston, IL (US)

( * ) Notice: Subject to any disclaimer, the term of this patent is extended or adjusted under 35 U.S.C. 154(b) by 0 days.

(21) Appl. No.: 09/330,905

(22) Filed: Jun. 11, 1999

(51) Int. Cl.[7] .............................................. A61K 31/70
(52) U.S. Cl. .......................................... 514/46; 514/43
(58) Field of Search ...................... 514/43, 46

(56) References Cited

U.S. PATENT DOCUMENTS

| | | | |
|---|---|---|---|
| 3,616,208 A | 10/1971 | Howells et al. | 195/28 N |
| 3,959,257 A | 5/1976 | Umezawa et al. | 260/211.5 R |
| 4,014,769 A | 3/1977 | Umezawa et al. | 204/158 R |
| 4,163,839 A | 8/1979 | Umezawa et al. | 536/24 |
| 4,315,920 A | 2/1982 | Schaeffer et al. | 424/180 |
| 4,861,873 A | 8/1989 | Robins et al. | 536/27 |
| 4,880,918 A | 11/1989 | Rapaport | 536/27 |
| 4,912,092 A | 3/1990 | Gruber | 514/45 |
| 4,996,308 A | 2/1991 | Edwards et al. | 536/26 |
| 4,997,924 A | 3/1991 | Jarvi et al. | 536/26 |
| 5,049,372 A | 9/1991 | Rapaport | 424/1.1 |
| 5,180,714 A | 1/1993 | Sufrin et al. | 514/46 |
| 5,227,371 A | 7/1993 | Rapaport | 514/46 |
| 5,415,873 A | 5/1995 | Trepel et al. | 424/422 |
| 5,641,500 A | 6/1997 | Trepel et al. | 424/422 |
| 5,663,155 A | 9/1997 | McCaffrey et al. | 514/45 |
| 5,679,648 A | 10/1997 | McCaffrey et al. | 514/46 |
| 5,705,491 A | 1/1998 | Yamada | 514/46 |
| 5,731,432 A | 3/1998 | Erion et al. | 540/568 |
| 5,763,597 A | 6/1998 | Ugarkar et al. | 536/27.13 |
| 5,773,603 A | 6/1998 | Yamada | 514/46 |
| 5,773,607 A | 6/1998 | Takeuchi et al. | 536/124 |
| 5,780,450 A | 7/1998 | Shade | 514/46 |
| 5,795,977 A | 8/1998 | Ugarkar et al. | 536/27.13 |
| 5,864,033 A | 1/1999 | Browne et al. | 536/27.13 |
| 5,886,167 A | 3/1999 | Takeuchi et al. | 536/27.21 |
| 5,886,195 A | 3/1999 | Tang et al. | 549/75 |

FOREIGN PATENT DOCUMENTS

| | | | |
|---|---|---|---|
| EP | 0 079 054 A1 | 5/1983 | A61K/31/70 |
| EP | 0 365 849 A2 | 5/1990 | C07H/19/16 |
| RU | 2071770 | * 1/1997 | A61K/31/675 |
| RU | 2071771 | 1/1997 | A61K/31/675 |
| WO | WO 94/18200 | 8/1994 | C07D/487/04 |
| WO | WO 96/16664 | 6/1996 | 514/46 |
| WO | WO96/16664 | * 6/1996 | 514/46 |

OTHER PUBLICATIONS

Ishii, Annu. Rep. Inst. Virus Res., 21, pp 55–57 Abstract Only, 1979.*
Zhao et al., Fujita Gakuen Igakkaishi, 7(1), pp 61–65 Abstract Only, 1979.*

Stedman's Medical Dictionary, 24th Edition, Feb. 24, 1983, pp. 223–224.*
Abbracchio et al., "A Novel Action for Adenosine: Apoptosis of Astroglial Cells in Rat Brain Primary Cultures," *Biochemical and Biophysical Research Communications*, 213(3):908–915 (Aug., 1995).
Agarwal, R. P., "Deoxycoformycin Toxicity in Mice After Long–term Treatment," *Cancer Chemother. Pharmacol.*, 5:83–87 (1980).
Agarwal, R. P., "In Vivo Inhibition of Adenosine Deaminase By 2'–Deoxycoformycin in Mouse Blood and Leukemia L1210 Cells," *Biochemical Pharmacology*, 29:187–193 (1980).
Agarwal, R. P., "Inhibitors of Adenosine Deaminase," *Pharmac. Ther.*, 17:399–429 (1982).
Agarwal et al., "Tight–binding inhibitors –IV. Inhibition of adenosine deaminases by various inhibitors" *Biochem. Pharmacol.* 26: 359–367 (1977).
Archer et al., "An Analysis of Multiple Mechanisms of Adenosine Toxicity in Baby Hamster Kidney Cells," *J. Cellular Physiology*, 124:226–232 (1985).
Aye et al., "Effect of 2'–Deoxycoformycin on Erythroid, Granulocytic, and T–Lymphocyte Colony Growth," *Blood*, 58(5):1043–1046 (Nov., 1981).
Begleiter et al., "Enhanced Cytotoxicity and Inhibition of DNA Damage Repair in Irradiated Murine L5178Y Lymphoblasts and Human Chronic Lymphocytic Leukemia Cells Treated with 2'–Deoxycoformycin and Deoxyadenosine in Vitro," *Cancer Research*, 48:3981–3986 (Jul., 1988).
Blake et al., "The Use of Adenosine Deaminase Assays in the Diagnosis of Tuberculosis," *SA Medical Journal*, 62: 19 (Jul., 1982).
Blay et al., "The Extracellular Fluid of Solid Carcinomas Contains Immunosuppressive Concentrations of Adenosine," *Cancer Research*, 57:2602–2605 (Jul., 1997).
Bontemps et al., "Evidence for a substrate cycle between AMP and adenosine in isolated hepatocytes" *Proc. Natl. Acad. Sci. USA*, 80: 2829–2833 (1983).
Brogden et al., "Pentostatin. A review of its pharmacodynamic and pharmacokinetic properties, and therapeutic potential in lymphoproliferative disorders," *Drugs*, 46(4):652–677 (Oct. 1993).
Bynum, J.W., "Characterization of Adenosine–induced Cytostasis in Melanoma Cells," *Cancer Research*, 40: 2147–2152 (Jul., 1980).

(List continued on next page.)

Primary Examiner—Jerome D. Goldberg
(74) Attorney, Agent, or Firm—Marshall, Gerstein & Borun

(57) ABSTRACT

The present invention provides materials and methods for the treatment of neoplastic disease states, especially cancers of cells/organs of epithelial origin. For example, the invention provides combination chemotherapy materials and methods for treatment comprising a first agent comprising adenosine or an adenosine derivative and a second agent comprising an inhibitor of at least one of the enzymes adenosine deaminase and AMP deaminase.

21 Claims, 6 Drawing Sheets

OTHER PUBLICATIONS

Camici et al., "Purine Enzyme Profile in Human Colon–Carcinoma Cell Lines and Differential Sensitivity to Deoxycoformycin and 2'–Deoxyadenosine in Combination," *Int. J. Cancer,* 62: 176–183 (1995).

Cha, S. et al., "Tight–binding inhibitors–II. Non–steady state nature of inhibition of milk xanthine oxidase by allopurinol and alloxanthine and of human erythrocytic adenosine deaminase by coformycin" *Biochem. Pharmacol.* 24: 2187–2197 (1975).

Cheson, B.D., "Infectious and immunosuppressive complications of purine analog therapy," *Journal Clinical Oncology,* 13(9):2431–2448 (Sep., 1995).

Cheson, B.D., "Neurotoxicity of purine analogs: A review," *Journal Clinical Oncology,* 12(10):2216–2228 (Oct., 1994).

Cheson, B.D., "New Antimetabolites in the Treatment of Human Malignancies," *Seminars in Oncology,* 19(6):695–706 (Dec., 1992).

Cheson, B.D., "Perspectives on Purine Analogues," *Hematol Cell Ther,* 38:S109–S116 (1996).

Constine et al., "Adenosine Deaminase Inhibitors: Differential Effects on Multiple Forms of Adenosine Deaminase," *Biochemical and Biophysical Research Communications,* 85(1):198–202 (Nov., 1978).

Crabtree et al., "Reactivity with adenosine deaminase. Incorporation into intracellular nucleotides of human erythrocytes and L 1210 cells and cytotoxicity to L 1210 cells," *Biochemical Pharmacology,* 28:1491–1500 (1979).

Davies et al., "Studies of several pyrrolo [2,3–d] pyrimidine analogues of adenosine which lack significant agonist activity at A1 and A2 receptors but have potent pharmacological activity in vivo" *Biochem. Pharmacol.,* 35:3021–3029 (1986).

Dawicki et al., "Extracellular ATP and Adenosine Cause Apoptosis of Pulmonary Artery Endothelial Cells," *Am. J. Physiol.,* 273: L485–L494 (1997).

Debatisse et al., "The Potentiation of Adenine Toxicity to Chinese Hamster Cells by Coformycin: Suppression in Mutants with Altered Regulation of Purine Biosynthesis or Increased Adenylate–Deaminase Activity," *Journal Cellular Physiology,* 106(1):1–11 (Jan., 1981).

Dillman, R., "A New Chemotherapeutic Agent: Deoxycoformycin (Pentostatin)," *Seminars in Hematology,* 31(1): 16–27 (1994).

Dragunow and Faull, "Neuroprotective effects of adenosine" *Trends in Pharmacol. Sci.,* 9: 193 (1988).

Henderson et al., "Inhibitors of nucleoside and nucleotide metabolism" *Cancer Chemotherapy Rep. Part 2, 3:* 71–85 (1972).

Henderson et al., "Inhibition of Animal and Invertebrate Cell Growth by Naturally Occurring Purine Bases and Ribonucleosides," *Pharmacology & Therapeutics,* 8: 539–571 (1980).

Henderson et al., "Toxicity of Naturally Occurring Purine Deoxyribonucleosides," *Pharmacology & Therapeutics,* 8:573–604 (1980).

Hershfield et al., "Immunodeficiency Diseases Caused by Adenosine Deaminase Deficiency and Purine Nucleoside Phosphorylase Deficiency," in *The Metabolic Basis of Inherited Disease,* Chapter 52, Sixth Edition, Scriver et al., (Eds.), McGraw–Hill Information Services Company (1989).

Hershfield et al., "Resistance of an Adenosine Kinase–Deficient Human Lymphoblastoid Cell Line to Effects of Deoxyadenosine on Growth, S–Adenosyl–Homocysteine Hydrolase Inactivation, and dATP Accumulation," *Proc. Natl. Acad. Sci., USA,* 77(7):4292–4296 (Jul., 1980).

Kang et al., "Dipyridamole Enhancement of Toxicity to L1210 Cells by Deoxyadenosine and Deoxycoformycin Combinations in Vitro," *Cancer Research,* 44:461–466 (Feb., 1984).

Kredich et al., "S–Adenosylhomocysteine Toxicity in Normal and Adenosine Kinase–Deficient Lymphoblasts of Human Origin," *Proc. Natl. Acad. Sci., USA,* 76(5): 2450–2454 (May, 1979).

Kulkarni and Wakade, "Quantitative Analysis of Similarities and Differences in Neurotoxicities Caused by Adenosine and 2'–Deoxyadenosine in Sympathetic Neurons," *J. Neurochemistry,* 67(2): 778–786 (1996).

Lambe et al., "Pharmacokinetics of Inhibition of Adenosine Deaminase By Erythro–9–(2–Hydroxy–3–Nonyl)Adenine in CBA Mice," *Biochemical Pharmacology,* 31(4):535–539 (1982).

Lapi et al., "Toxicities of Adenosine and 2'–Deoxyadenosine in L Cells Treated with Inhibitors of Adenosine Deaminase," *Biochemical Pharmacology,* 26:71–76 (1977).

Major et al., "Clinical Pharmacology of Deoxycoformycin," *Blood,* 58(1):91 (Jul., 1981).

Miller et al., "Adenosine Kinase from Rabbit Liver." *J. Biol. Chem.,* 254: 2346–2352 (1979).

Mitchell et al., "Purinogenic Immunodeficiency Diseases: Selective Toxicity of Deoxyribonucleosides for T Cells," *Proc. Natl. Acad. Sci., USA,* 75(10):5011–5014 (Oct., 1978).

Olafsson et al., "Reduction of reperfusion injury in the canine preparation by intracoronary adenosine: Importance of the endothelium and the no–reflow phenomenon" *Circulation,* 76: 1135–1145 (1987).

O'Dwyer et al., "2' Deoxycoformycin (Pentostatin) for Lymphoid Malignancies," *Annals Int. Med.* 108: 733–743 (1988).

Plunkett and Gandhi, "Pharmacology of Purine Nucleoside Analogues," *Hematol. Cell Ther.* 38: S67–S74 (1996).

Prescott et al., "Inhibitors of adenosine Kinase by $\alpha$, $\omega$–Di(adenosin–$N^6$–yl) alkanes." *Nucleosides & Nucleotides,* 8: 297 (1989).

Ratech et al., "Effects of Deoxycoformycni in Mice. II. Differences between the drug sensitivities and purine metabolizing enzymes of transplantable lymphomas of varying immunologic phenotypes," *Journal Immunology,* 132(6):3077–3084 (Jun., 1984).

Rowland et al., "Adenosine Deaminase Gene Amplification in Deoxycoformycin–Resistant Mammalian Cells," *Archives Biochemistry Biophysics,* 239(2): 396–403 (1985).

Sawa et al., "Mode of Inhibition of Coformycin on Adenosine Deaminase," *Journal of Antibiotics, Ser. A, XX*(4):227 (1967).

Schaeffer et al., "Enzyme Inhibitors. 26. Bridging Hydrophobic and Hydrophilic Regions on Adenosine Deaminase with Some 9–(2–hydroxy–3–alkyl)Adenines," *Journal Medicinal Chemistry,* 17(1):6–8 (Jan., 1974).

Schaeffer et al., "Structure–activity Relationships in Adenosine Deaminase Inhibitors," *Journal Medicinal Chemistry,* 13(3):452–455 (May, 1970).

Shimazaki et al., "Synthesis of isocoformycin, an adenosine deaminase inhibitor of synthetic origin." *J. Antibiot. (Tokyo),* 32:537 (1979).

Shimazaki et al., "Studies of Inhibition of Adenosine Deaminase By Isocoformycin In Vitro and In Vivo," *Journal of Antibiotics*, p.654 (Jun., 1979).

Showalter et al., "Improved Production of Pentostatin and Identification of Fermentation Cometabolites," *Journal of Antibiotics*, 1914–1918 (Dec., 1992).

Siaw et al., In Vitro Metabolism of Deoxycoformycin in Human T Lymphoblastoid Cells,38 *Journal Biological Chemistry*, 259(15):9426–9433 (Aug., 1964).

Simmonds et al., "The Role for Purine Metabolism in the Immune Response: Adenosine–deaminase Activity and Deoxyadenosine Catabolism," *Lancet*, 1(8055):60–63 (Jan., 1978).

Smyth et al., "In vivo Toxicity to Lymphoid Tissue by 2'–Deoxycoformycin," *Cancer Chemother. Pharmacol.*, 1:49–51 (1978).

Spremulli et al., "2'–Deoxycoformycin–Induced Hemolysis in the Mouse," *JNCI*, 68(6):1011 (Jun., 1982).

Svendsen et al, "Synergistic Effect of 3'Deoxyadenosine $N^1$–Oxide and Adenosine Deaminase Inhibitors on Growth of Ehrlich Ascites Tumor Cells In Vivo," *Cancer Chemotherapy & Pharmacology* 21(1): 35–39 (1988).

Snyder et al., "Alternative Pathways of Deoxyadenosine and Adeonsine Metabolism," *Journal of Biological Chemistry*, 248(16):5899–5904 (Aug., 1973).

Snyder et al., "Cytotoxic and Metabolic Effects of Adenosine and Adenine on Human Lymphoblasts," *Cancer Research*, 38:2357–2362 (Aug., 1978).

Venner et al., "Levels of 2'–Deoxycoformycin, Adenosine, and Deoxyadenosine in Patients with Acute Lymphoblastic Leukemia," *Cancer Research*, 41(11 pt.1):4508–4511 (Nov., 1981).

Wakade et al., "Deoxynuceloside Induces Neuronal Apoptosis Independent of Neurotrophic Factors," *J. Biol. Chem.*, 270(30): 17986–17992 (Jul., 1995).

Wakade et al., "2'–Deoxyadenosine Induces Apoptosis in Rat Chromaffin Cells," *J. Neurochemistry* 67(6):2273–2281 (Dec., 1996).

Wang et al., "Inhibition of Growth and p21 $^{ras}$ Methylation in Vascular Endothelial Cells by Homocysteine but Not Cysteine," *J. Biological Chemistry*, 272(40): 25380–85 (Oct., 1997).

Woo et al., "A Novel Adenosine and Ara–A Deaminase Inhibitor, (R)–3–(2–Deoxy–β–D–erythro–pento–furanosyl)–3,6,7,8–tetrahydroimidazo[4,5–d][1,3]diazepin–8–ol," *J. Heterocyclic Chem.*, 11:641 (Aug., 1974).

Fishman, et al. "Adenosine and Other Low Molecular Weight Factors Released by Muscle Cells Inhibit Tumor Cell Growth," *Cancer Research* 58:3181–3187 (Jul. 15, 1998).

Fujimori, et al. "Enhancement of Cellular Adenosine Triphosphate Levels in PC12 Cells by Extracellular Adenosine", *Biol. Pharm. Bull.* 25(3): 307–311 (2002).

Hoskin, et al. "Adenosine as a possible inhibitor of killer T–cell activation in the microenvironment of solid tumours", *Int. J. Cancer: 59*, 854–855 (1994).

Hoskin, et al. "Adenosine Acts Through an $A_3$ Receptor to Prevent the Induction of Murine Anti–$CD_3$–Activated Killer T Cells", *Int. J. Cancer 99*: 386–395 (2002).

Mackenzie et al., "Adenosine Suppresses $\alpha_4\beta_7$ Integrin–Mediated Adhesion of T Lymphocytes to Colon Adenocarcinoma Cells", *Experimental Cell Research 276*, 90–100 (2002).

Schrier, et al., "Extracellular Adenosine–Induced Apoptosis in Mouse Neuroblastoma Cells–Studies on Involvement of Adenosine Receptors and Adenosine Uptake", *Biochemcial Pharmacology 61*: 417–425–(2001).

Spychala, J. "Tumor–promoting functions of adenosine," *Pharmacology & therapeutics* 87: 161–173 (2000).

Williams, et al. "Adenosine Acts through a Novel Extracellular Receptor to Inhibit Granule Exocytosis by Natural Killer Cells," *Biochemical and Biophysical Research Communications 231*: 264–269 (1997).

Dale, N., "Rapid Report: Delayed Production of Adenosine Uderlies Temporasl Modulation of Swimming in Frog Embryo," *Journal of Physiology*, 511.1:265–272 (1998).

Dale et al., "Direct Measurement of Adenosine Release During Hypoxia in the CA1 Region of the Rat Hippocampal Slice," *Journal of Physiology*, 526.l:143–155 (2000).

Di Pierro et al., "An Ion–Pairing High–Performance Liquid Chromatographic Method for the Direct Simultaneous Determination of Nucleotides, Deoxynucleotides, Nicotinic Cyonzymes, Oxypurines, Nucleosides, and Bases in Perchloric Acid Cell Extracts," *Analytical Biochemistry*, 231:407–412 (1995).

Mubagwa et al., "Adenosine, Adenosine Receptors and Myocardial Protection: An Updated Overview," *Cardiovascular Research*, 52: 25–39 (2001).

Schrier et al., "Extracellular Adenosine–Induced Apoptosis in Mouse Neuroblastoma Cells–Studies on Involvement of Adenosine Receptors and Adenosine Uptake", *Biochemcial Pharmacology*, 61: 417–425–(2001).

Spychala, J., "Tumor–promoting functions of adenosine," *Pharmacology & Therapeutics*, 87: 161–173 (2000).

Williams et al., "Adenosine Acts through a Novel Extracellular Receptor to Inhibit Granule Exocytosis by Natural Killer Cells," *Biochemical and Biophysical Research Communications*, 231: 264–269 (1997).

Fishman et al., "Adenosine Acts as an Inhibitor of Lymphoma Cell Growth: A Major Role for the A3 Adenosine Receptor," *Eur. J. Cancer*, 36:1452–1458 (2000).

* cited by examiner

COMBINATION CANCER THERAPY COMPRISING ADENOSINE AND DEAMINASE ENZYME INHIBITORS

FIELD OF THE INVENTION

The present invention relates generally to the field of medicine. More particularly, the invention relates to the field of oncology, especially the treatment of cancers of an epithelial origin.

DESCRIPTION OF RELATED ART

Purine nucleosides (e.g., adenosine, deoxyadenosine, guanosine, deoxyguanosine), which comprise bi-cyclic nitrogenous purine bases (adenine, guanine) linked to a pentose sugar (ribose, deoxyribose), are found in all cell types, e.g., serving as constituent nucleosides of both ribonucleic acid (RNA) and deoxyribonucleic acid (DNA). At high concentrations, purines and their derivatives have been shown to arrest normal cell growth and cause apoptosis in certain cell types, such as endothelial cells, macrophages, and lymphocytes. It has been hypothesized that cell death usually occurs through conversion of adenosine into nucleotides (via phosphorylation) and/or into S-adenosylhomocysteine, which in turn induce pyrimidine starvation or inhibit cellular methylation. The high concentrations of adenosine necessary to cause cell death are difficult to maintain, however, due to the many cellular processes by which adenosine can be converted to other products. See Bynum, Cancer Res. 40: 2147–2152 (1980); Archer et al., J. Cell. Phys. 124:226–232 (1985); Henderson et al., Pharmac.& Ther. 8: 539–571 and 573–604 (1980).

Adenosine (Ado) is reportedly released from cells in response to alterations in oxygen supply or demand, and has been reported to be a potent vasodilator involved in the metabolic regulation of blood flow. At less than toxic concentrations, adenosine has been reported to have both cardio-protective and neuro-protective properties [Olafsson et al., Circulation, 76: 1135–1145 (1987); Dragunow and Faull, Trends in Pharmacol Sci., 9: 193 (1988).]

Adenosine deaminase (ADA) is the hydrolytic enzyme that catalyzes the deamination of adenosine and deoxyadenosine to inosine and deoxyinosine, and thus is one of the enzymes involved in controlling adenosine/deoxyadenosine levels. ADA is found at especially high levels in the spleen, thymus, and B and T lymphocytes. Adenosine monophosphate deaminase (AMP deaminase, AMPDA) is functionally related to adenosine deaminase, converting adenosine monophosphate to inosine monophosphate. ADA plays an essential role in leukocytes and its absence is associated with a severe, inherited combined immunodeficiency disease.

Interestingly, although ADA is capable of deaminating both adenosine and 2-deoxyodenosine (dAdo), it is principally dAdo that accumulates in plasma following dosing with an ADA inhibitor, such as deoxycoformycin (dCF). Apparently, deamination of adenosine occurs principally at the monophosphate level by the enzyme AMP deaminase. The dAMP moiety is a poor substrate for AMP deaminase, so deamination of dAdo is largely dependent on ADA, and ADA-inhibition results in dAdo accumulation. [Plunkett and Gandhi, Hematol. Cell Ther. 38: S67–S74 (1996).]

Inhibitors of ADA have been recognized as potential immunosuppressive agents, and many early studies of the cytotoxicity of adenosine deaminase inhibitors have involved human lymphocytes. [See, e.g., O'Dwyer et al., Annals Int. Med. 108: 733–743 (1988).] For example, dCF, a powerful ADA inhibitor ($K_i$ for erythrocyte ADA of $2 \times 10^{-12}$), has been used to treat lymphatic leukemias and is FDA-approved (Pentostatin) to treat hairy cell leukemia. Coformycin, the ribosyl analog of dCF, also acts as an ADA inhibitor. The pharmacology and efficacy of dCF and two other prominent nucleoside analogs 2-chlorodeoxyadenosine, (CDA, cladribine) and arabinosyl-2-fluoroadenine monophosphate (F—ara—AMP, fludarabine) for treating lymphoid malignancies are reviewed in Plunkett and Gandhi, Hematol. Cell Ther. 38: S67–S74 (1996), and Diliman, R., Seminars in Hematoloogy, 31: 16–27 (1994), incorporated herein by reference. The toxicity of ADA inhibitor compounds appears to relate to their causing an accumulation of toxic intracellular levels of dAdo, which (through conversion to dATP via successive phosphorylations) inhibits ribonucleotide reductase. The lethal effects of dAdo on blood cells has been extensively studied and reported in the literature.

Not all of the studies involving ADA inhibitors have focused on lymphoid malignancies. Camici et al., Int. J. Cancer, 62: 176–183 (1995) reported an assessment of the effect of deoxycoformycin (.001 to 1 $\mu$M) and 2'-deoxyadenosine (0 to 500 $\mu$M) on the growth of two cultured human colon carcinoma cell lines and on Chinese hamster ovary (CHO K-I) cells. Neither compound was reported to be toxic when used alone, whereas their combination was reported to cause cell growth inhibition, with the CHO cells more sensitive than the colon carcinoma cells. At the concentrations tested, 50–150 $\mu$M deoxyadenosine was required to approach full cell growth inhibition. The authors suggest that phosphorylation of deoxyadenosine by adenosine kinase plays a central role in the toxicity of the combination therapy, and observed that the cytotoxic effect was almost completely reversed in the three cell lines when inhibitors of adenosine kinase were added to the cell culture medium. Introduction of dipyridamole to inhibit deoxyadenosine uptake also was reported to reverse the toxicity.

Svendsen et al., Cancer Chemotherapy & Pharmacology 21(1): 35–39 (1988) reported that simultaneous administration of 3'deoxadenosine N1-oxide and either ERNA or dCF to mice bearing Ehrlich ascites tumor cells resistant to 3'-deoxyadenosine N1-oxide resulted in 80–90% inhibition of tumor growth in vivo.

Rowland et al., Arch. Biochem. Biophys., 239(2): 396–403 (1985) developed a rat hepatoma cell line that was ADA-dependent and dCF sensitive. The authors observed that dCF-resistant variants developed and determined that such cells have progressively increasing concentrations of ADA activity, apparently resulting from ADA gene amplification. A dCF-resistant CHO cell line developed by the authors also demonstrated extreme increases in ADA activity, but this change was not attributable to gene amplification.

Wakade et al., J. Biol. Chem., 270(30): 17986–17992 (1995) have shown that dAdo (which increases in concentration in the presence of an ADA inhibitor) causes neuronal cell toxicity in a dose-dependent manner (maximal at 300 $\mu$M). Neuronal death was correlated to a dramatic increase in the dATP content of the neurons. Nanomolar concentrations of 5'-Iodotubercidin (ITu) were reported to completely and dose-dependently inhibit formation of dATP and protect against toxicity of sub-millimolar concentrations of dAdo. Interestingly, neither dCF nor another ADA inhibitor [erythro-9-(2-hydroxy-3-nonyl) adenine (EHNA)] at concentrations of 3–30 $\mu$M were found to modify the toxic effects of dAdo in the neuronal model. [See also Kulkarni and Wakade, J. Neurochem., 67(2): 778–786 (1996).]

Wakade et al., *J. Neurochemistry* 67(6):2273–2281 (December, 1996) reported that 100 $\mu$M dAdo (but not adenosine) in combination with 3 $\mu$M dCF was toxic to chromaffin cells. The toxicity, which was associated with dATP accumulation, was eliminated by co-culture with nanomolar concentrations of ITu.

There also exists suggestions in the literature for using AMP deaminase inhibitors for therapeutic purposes. For example, Gruber and colleagues have suggested using AMP deaminase inhibitors to treat or prevent a variety of cardiovascular and other disorders. [See U.S. Pat. Nos. 5,731,432 and 4,912,092.]

The treatment of parasitic (e.g., fungal, trypanosomal) infections with ADA inhibitors in combination with 3'-deoxypurine nucleosides (e.g., cordycepin) has been suggested. See McCaffrey et al., U.S. Pat. Nos. 5,679,648 and 5,663,155 and International Patent Publication No. WO 96/16664.

Extracellular adenosine and adenosine triphosphate (ATP) have also been reported to cause cytotoxicity. For example, Dawicki et al., *Am. J. Physiol.,* 273: L485–L494 (1997) reviewed literature reporting ATP-induced apoptosis in lymphocytes, and reported that extracellular ATP, ADP, AMP, adenosine, and non-metabolized adenosine analogs [3-deaxaadenosine and Z-5'-fluoro-4',5'-didehydro-5'-deoxyadenosine (MDL-28842)] caused apoptosis of pulmonary artery endothelial cells. The authors concluded that the ATP metabolite adenosine was responsible for the observed toxicity, since adenosine itself and nucleotides that are degraded to adenosine caused DNA damage, whereas non-metabolizable ATP analogs (e.g., ATP$\gamma$S) and several adenosine metabolites did not. The extracellular ATP-induced cleavage (observed at 10 $\mu$M ATP, statistically significant at 100 $\mu$M) was reportedly prevented by the nucleoside transport inhibitor dipyridamole.

Bynum, J. W., *Cancer Res.,* 40: 2147–2152 (Jul., 1980) reported that mouse melanoma cells were "moderately sensitive" to adenosine, with 80% growth inhibition being observed at 50 $\mu$M, compared to 5 $\mu$M or 400 $\mu$M reportedly required to achieve similar effects in lymphoid cells and fibroblasts, respectively. The different sensitivities were not attributed to ADA, because the lymphoid cells had two to four times the level of ADA activity than the melanoma cells or fibroblasts. The authors suggested that adenosine's toxicity may be caused by interruption of pyrimidine biosynthesis and resultant depletion of pyrimidines. Guanosine also reportedly possessed growth-inhibitory properties. The author reported that homocysteine thiolactone (HCT) enhanced the cytotoxicity of adenosine, but not of guanosine. See also Archer et al., *J. Cell. Physiol.,* 124: 226–232 (1985).

Homocysteine is a compound which, in high concentrations, has been identified as a prevalent risk factor for myocardial infarction and stroke. Wang et al., *J. Biol. Chem.,* 272(40): 25380–85 (Oct., 1997) reported that homocysteine (10–50 $\mu$M, a range that overlaps levels observed clinically) caused inhibition of DNA synthesis in vascular endothelial cells and arrested their growth at the $G_1$ phase of the cell cycle, which may play an important role in the arteriosclerotic disease process. Kredich et al., *Proc. Natl. Acad. Sci. USA,* 76(5): 2450–2454 (1979) reported that addition of 100 $\mu$M L-homocysteine thiolactone to cells treated with the ADA inhibitor EHNA and adenosine had the effect of enhancing adenosine toxicity towards a human lymphoblast cell line.

Yet another body of research has focused on use of purine nucleotides or hydrolysis-resistant purine nucleotide analogs as anti-neoplastic agents. For example, Trepel et al., U.S. Pat. Nos. 5,415,873 and 5,641,500, report that certain hormone-independent prostatic tumor cell lines express a $P_2$ subtype purinergic receptor which interact with ATP, and that such growth of such cell lines is inhibited by ATP. Adenosine, which lacks phosphate moieties, is reported to be from about 40-fold to about 500-fold less potent an agonist than ATP of these cell types.

In U.S. Pat. No. 5,227,371, Rapaport reports that adenine nucleotide or adenosine plus inorganic phosphate, but not adenosine alone, yields a sustained "secondary wave" of extracellular blood plasma ATP levels. Rapaport suggests that extracellular ATP increases may have several beneficial effects, including tumor growth inhibition. In U.S. Pat. Nos. 5,049,372 and 4,880,918, Rapaport suggests that ATP or ADP can be used as selective tumor growth inhibition agents, whereas purines will inhibit the growth not only of tumor cells but also of normal cells. Rapaport's explanation is that ADP or ATP penetrate the plasma membrane of tumor cells, but not normal cells, without degradation to AMP or adenosine. Rapaport explicitly states that the observed effects on cellular growth is unique to ADP and ATP and cannot be duplicated by adenosine.

Thus, purine nucleosides, purine nucleotides, derivatives thereof, and ADA inhibitors have been investigated by several research groups and, in some instances such as the treatment of hairy cell leukemia with dCF, have shown limited success. However, neoplastic diseases (e.g., cancer) remain one of the leading killers in modern societies, and a long felt need exists for new therapeutic regimens to treat neoplastic diseases, especially non-lymphoid related neoplastic diseases. A long felt need also exists for effective treatments which can be carefully controlled and modulated to maintain efficacy and minimize toxicity to the patient's non-cancerous tissues and cells.

SUMMARY OF THE INVENTION

The present invention provides novel chemotherapeutic materials and methods that address one or more of the foregoing long felt needs.

In particular, the present invention provides materials and methods for the treatment of neoplastic disease states, especially cancers of cells/organs of epithelial origin. For example, the invention provides combination chemotherapy materials and methods for treatment comprising a first agent comprising adenosine or an adenosine derivative and a second agent comprising an inhibitor of at least one of the enzymes adenosine deaminase and AMP deaminase.

In one embodiment, the invention provides a composition comprising: a first compound selected from the group consisting of adenosine, adenosine derivatives, and pharmaceutically acceptable salts thereof, in admixture with a second compound selected from the group consisting of adenosine deaminase inhibitors (ADAI), adenosine monophosphate deaminase inhibitors (AMPDAI), and pharmaceutically acceptable salts thereof. Since the composition is useful for medical treatment, in a preferred embodiment it also comprises a pharmaceutically acceptable carrier. The composition may further include additional therapeutic agents, such as homocysteine compounds that potentiate the effects of the first two compounds, and/or additional agents such as preservatives and the like. ADAI and AMPDAI compounds whose inhibitory activities are characterized by sub-nanomolar inhibition constants ($K_i \leq 1$ nM) are preferred. In one preferred variation, the second compound of the composition has dual activities as both an ADAI and an AMP- DAI. In another variation, the second compound is an ADAI, and the composition further includes a third compound that is an AMPDAI.

In a related embodiment, the invention provides a unit dose comprising: a first composition comprising a member selected from the group consisting of adenosine, adenosine derivatives, and pharmaceutically acceptable salts thereof, and a second composition comprising a member selected from the group consisting of adenosine deaminase inhibitors, adenosine monophosphate deaminase inhibitors, and pharmaceutically acceptable salts thereof. The compositions are preferably included in the unit dose at concentrations effective to inhibit the growth of neoplastic cells in a cancer patient.

In one variation, the unit dose is formulated wherein the first and second compositions are in admixture with each other. Preferably this mixture further includes a pharmaceutically acceptable carrier. In yet another variation, the unit dose is formulated such that the first and second compositions are packaged together as a kit, but are not in admixture. Separate packaging of the two compositions permits administration by separate routes, at separate times, and/or at separate rates, and permits formulating each composition uniquely.

In a preferred embodiment, the unit dose is packaged as kit with one or more additional compositions that are useful for enhancing the treatment regimen of a cancer patient. For example, the unit dose further includes a composition that comprises homocysteine in an amount effective to potentiate the anti-neoplastic activity of the first and second compositions.

In a highly preferred embodiment, the unit dose further includes a composition that comprises a protective agent such as a nucleoside transport inhibitors or adenosine kinase inhibitor. It is contemplated that the two or more anti-neoplastic therapeutic agents are administered via a route designed to achieve high concentrations at the site of a tumor, whereas the protective agent(s) is administered systemically to protect healthy (non-cancerous) tissues from the anti-neoplastic agents.

The invention also provides for methods of treatment that involve administration of compounds, compositions, and unit doses of the invention for the treatment of disease states, particularly neoplastic disease states. For example, the invention provides a method of treating a neoplastic disease state in a patient in need of such treatment, comprising the steps of: administering to a patient suffering from a neoplastic disease state a first compound selected from the group consisting of adenosine, adenosine derivatives, and pharmaceutically acceptable salts thereof, and a second compound selected from the group consisting of adenosine deaminase inhibitors (ADAI), adenosine monophosphate deaminase inhibitors (AMPDAI), and pharmaceutically acceptable salts thereof As explained below, treatment of malignancies of epithelial cell origin, such as those of the lungs, breasts, gastrointestinal system, genitorurinary tract, or reproductive organs is specifically contemplated. A highly preferred embodiment involves treatment of ovarian cancers.

In one variation, the method of treatment involves administering one or more of the anti-neoplastic compounds in a manner that generates high concentrations in or around the tumor area, and administering protective agents systemically to protect the patient's healthy tissues and cells, including the heart, against toxic side-effects of the anti-neoplastic compounds.

Additional features and variations of the invention will be apparent to those skilled in the art from the entirety of this application, including the drawing and detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

In addition to the foregoing, the invention includes, as an additional aspect, all embodiments of the invention narrower in scope in any way than the variations specifically mentioned herein. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION OF THE INVENTION

Figure 1:
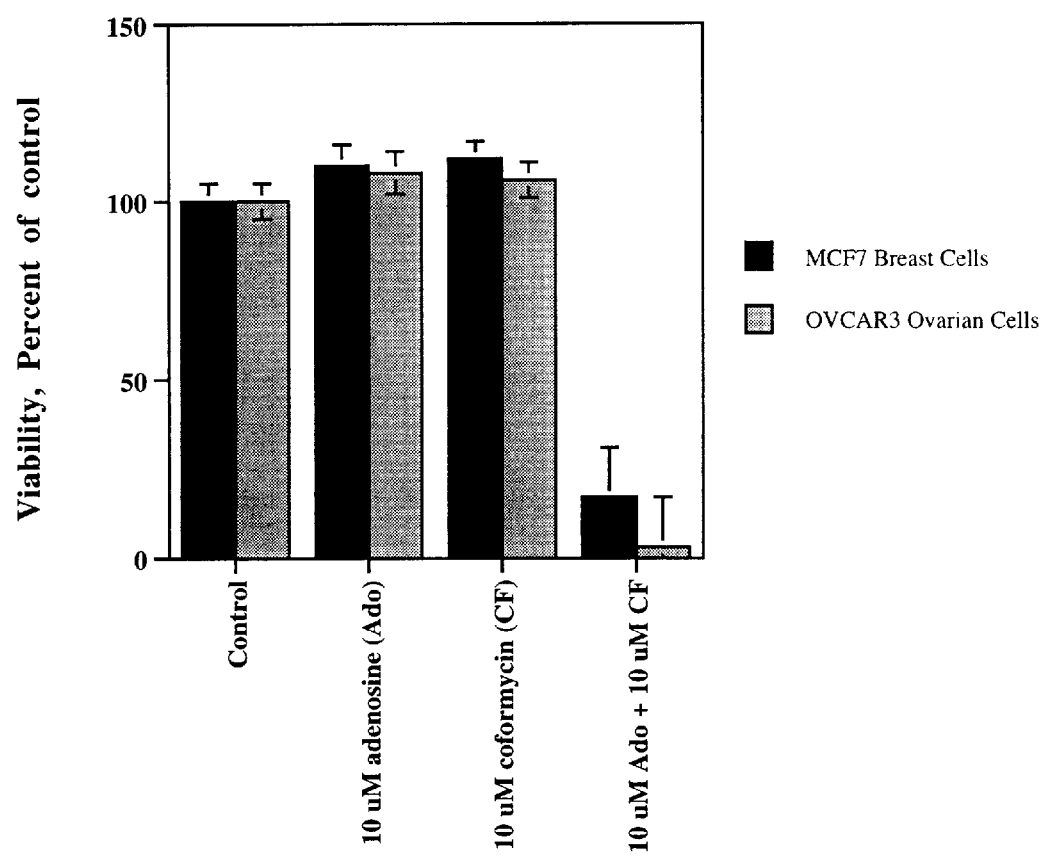
FIG. 1 is a bar graph depicting the efficacy of adenosine, coformycin, and the combination thereof for killing breast cancer (MCF7) and ovarian cancer (OVCAR3) cell lines. The results are presented as the percent of viable (surviving) cells (compared to an untreated control) following a sixty hour treatment regimen.

The invention provides a composition comprising: a first compound selected from the group consisting of adenosine, adenosine derivatives, and pharmaceutically acceptable salts thereof, in admixture with a second compound selected from the group consisting of adenosine deaminase inhibitors (ADAI), adenosine monophosphate deaminase inhibitors (AMPDAI), and pharmaceutically acceptable salts thereof As described herein in detail, such compositions are considered useful for the treatment of neoplastic diseases. Therefore, the composition preferably contains the compounds at a therapeutically effective molar ratio. In a preferred embodiment, the molar ratio of the two compounds is 0.01 to 100; in a highly preferred embodiment 0.1 to 10; and in a very highly preferred embodiment, about 1.0.

Adenosine, as explained above, is a naturally occurring nucleoside comprised of the purine adenine linked to ribose, and is involved in numerous vital biological processes in all organisms, including metabolic processes and synthesis of nucleic acids. Adenosine is commercially available from numerous commercial suppliers and is FDA-approved for use in human patients.

The term "adenosine derivative" is intended to encompass:

(1) compounds comprising a pentose ring (including but not limited to ribose and deoxyribose) coupled to a purine (e.g., adenine, guanine) base;

(2) compounds as set forth in (1) which further include additions, deletions, and/or substitutions at the 2' or 3' positions of the ribose ring or at any site on the adenine rings. Additions or substitutions with chemical moieties including hydrogen, hydroxyl, halogens, $C_1$–$C_6$ alkyls and alkoxyls, amines, amides, sulfbydrals, sulfinyls, sulfonyls, nitryls, phosphoryls, and combinations of the foregoing are contemplated. Compounds having one, two, three, four, or five, or six such substitutions are explicitly contemplated. Cordycepin (3'-deoxyadenosine) and cordycepin derivatives are specifically contemplated; and (3) "pro-drugs" that, when administered to patients, are metabolized or altered in vivo into adenosine or adenosine derivatives as set forth in (1) or (2). For example, mono- di- and tri-phosphate nucleotides of adenosine or adenosine derivatives are contemplated.

Compositions of the invention preferably contain adenosine or an adenosine derivative at a concentration of between about 1.0 nM to 100 mM; and more preferably 100 nM to 10 mM; and still more preferably 10 $\mu$M to 10 $\mu$M. Higher concentration compositions may be preferred for shipping and/or storage and may be diluted with pharmaceutically acceptable diluents, adjuvants, excipients, carriers, or the like prior to administration to patients.

The adenosine dearninase inhibitors or adenosine monophosphate deaminase inhibitors may be any compound that prevents adenosine deaminase and/or adenylate (AMP) deaminase enzymes from deaminating their respective substrates. Inhibitors that demonstrate specificity for such deaminase enzymes and that do not interfere with unrelated cellular processes are preferred. As set forth below, inhibitors such as coformycin that exhibit greater inhibitory activity toward AMPDA are highly preferred. The terms "adenosine dearinase inhibitor" and "AMP deaminase inhibitor" are also intended to include "pro-drugs" that, when administered to patients, are metabolized or altered in vivo into compounds that act as ADAI's or AMPDAI's.

The literature contains numerous descriptions of deaminase inhibitors that are suitable for use in the present invention. For example, the production of the ADAI/AMPDAI coformycin is described in Umezawa et al., U.S. Pat. Nos. 4,014,769 and 3,959,257; Umezawa et al., U.S. Pat. No. 4,163,839 and Shimazaki et al., *J. Antibiot. (Tokyo)*, 32:537 (1979) describe the ADA inhibitor isocoformycin (a structural isomer of coformycin); Erion et al., U.S. Pat. No. 5,731,432, International Patent Publication No. WO 94/18200, and Gruber U.S. Pat. No. 4,912,092 describe AMPDA inhibitors; Schaeffer et al., U.S. Pat. No. 4,315,920, describes adenosine deaminase inhibitors that are derivatives of 9-alkyladenines, such as 9-(2-hydroxy-3-alkyl) adenines, e.g., EHNA; Takeuchi et al., U.S. Pat. Nos. 5,886,167 and 5,773,607 describe 2'-fluoro derivatives of coformycin with high ADA-inhibitory activity; Yamada, U.S. Pat. Nos. 5,773,603 and 5,705,491 describes ADA inhibitors comprising an O-alkylated moiety. A process for large-scale isolation of 2'-deoxycoformycin is described in Showalter et al., *J. Antibiotics*, 45:1914–1918 (Dec., 1992). All of the foregoing documents are incorporated herein by reference in their entirety.

Since compositions of the invention are intended for administration to humans or animals for medical purposes, it will be appreciated that, in a preferred embodiment, compositions of the invention further comprise a pharmaceutically acceptable carrier. Such carriers may be any solid, liquid, or gaseous materials useful for the purpose of administering a medicament to a patient. Pharmaceutically acceptable carriers are preferably sterile, inert, non-toxic, and compatible with the active ingredients of the composition. Carriers include diluents or vehicles such as fillers, binding agents, disintegrators, and lubricants. Exemplary carriers include lactose, saccharose, sodium chloride, potassium phosphate, glucose, starch, calcium carbonate, crystal cellulose or silicic acid, water, ethanol, propanol, gelatins, caraboxylmethyl cellulose, methyl cellulose, sodium alginate, agar, sodium hydrogencarbonate, calcium carbonate, stearic acid monoglyceride, stearates, boric acid powders, solid polyethylene glycol, polyoxyethylene sorbit, solutions and suspensions of any of the foregoing, glycerine, oils, fatty acid esters, and the like. The compositions of the invention also may contain other active ingredients such as preservatives.

The compositions may take any conventional pharmaceutical form, including that of a solution, emulsion, suspension, ointment, cream, granule, powder, spray, tablet, capsule, lozenge, or suppository. One or more of the administered compounds may be encapsulated, e.g., in liposomes, to facilitate intracellular delivery.

It is further contemplated that compositions of the invention may be formulated to include additional agents that will enhance the anti-neoplastic efficacy of the first and second compounds. For example, in a preferred embodiment, the composition further includes a homocysteine formulation, such as homocysteine thiolactone, at a concentration effective to enhance the toxicity of the composition towards tumors. For example, a molar ratio of adenosine: homocysteine of 0.01 to 1000 is contemplated, and a ratio of 1 to 100 is preferred. Moreover, the addition of other anti-neoplastic agents to the composition that improve therapeutic efficacy via a mechanism entirely independent of the first and second compounds is nonetheless considered within the scope of the invention.

In a related embodiment, the invention provides a unit dose comprising: a first composition comprising a member selected from the group consisting of adenosine, adenosine derivatives, and pharmaceutically acceptable salts thereof, and a second composition comprising a member selected from the group consisting of adenosine deaminase inhibitors, adenosine monophosphate deaminase inhibitors, and pharmaceutically acceptable salts thereof. In a preferred embodiment, the compositions are included in the unit dose at concentrations such that, when administered to a patient singly or repetitively, the unit dose will be effective to inhibit the growth of neoplastic cells in the patient. In preferred embodiments, the unit dose will be effective to kill the neoplastic cells.

In one variation, the unit dose is formulated wherein the first and second compositions are in admixture with each other. Preferably this mixture further includes a pharmaceutically acceptable carrier.

In yet another variation, the unit dose is formulated such that the first and second compositions are packaged together as a kit, but are not in admixture. A kit that includes each therapeutic agent packaged together in dosage form adds convenience to medical practitioners. Separate packaging of the two compositions permits administration by separate routes, at separate times, and/or at separate rates. Separate packaging also permits formulating each composition uniquely, e.g., with its own carriers and preservatives, to optimize shelf life and the like.

In a preferred embodiment (for both of the aforementioned variations), the unit dose of the invention is packaged as kit with one or more additional compositions that are useful for enhancing the treatment regimen of the patient. For example, the unit dose further includes a composition that comprises homocysteine in an amount effective to potentiate the anti-neoplastic activity of the first and second compositions.

In a highly preferred embodiment, the unit dose further includes a composition that comprises a protective agent to protect cells from the cytotoxic effects of the first and second compositions. In a preferred embodiment, the protective agent is selected from the group consisting of nucleoside transport inhibitors, adenosine kinase inhibitors, and pharmaceutically acceptable salts thereof. Thus, in one treatment regimen of the invention, the two or more anti-neoplastic therapeutic agents are administered via a route designed to achieve high concentrations at the site of a tumor, whereas the protective agent is administered systemically to protect healthy (non-cancerous) organs (e.g., heart), tissues, or cells (e.g., lymphoid cells) from the anti-neoplastic agents. For example, to treat non-metastasized ovarian cancer, the therapeutic agents are delivered intraperitoneally, e.g., via a series of injections or via a drug delivery pump. The protective agents is delivered intra-arterially or intravenously.

Nucleoside transport inhibitors that inhibit cellular uptake of adenosine (adenosine uptake inhibitors) and thereby protect cells from the potentially toxic effects of high adenosine concentrations comprise a first class of protective agent. Many adenosine uptake inhibitors have been described in the literature, including dipyridamole, propentofylline, dilazep, nitrobenzylthioinosine, S-(4-nitrobenzyl)-6-thioguanosine, S-(4-nitrobenzyl)-6-thioinosine, iodohydroxy-nitrobenzylthioinosine, and mioflazine. These agents, as well as methods for elucidating additional adenosine uptake inhibitors, are described in Shade, U.S. Pat. No. 5,780,450, incorporated herein by reference. In a preferred embodiment, the nucleoside transport inhibitor is dipyridimole, which is commercially available from Boehringer Ingelheim. Any compound that displays nucleoside transport inhibitor activity at concentrations that are themselves non-toxic to the host are considered appropriate for use in the invention.

Adenosine kinase catalyzes the phosphorylation of adenosine or deoxyadenosine, and in doing so is postulated to play a central role in the toxicity of adenosine or deoxyadenosine. Therefore, adenosine kinase inhibitors (compounds that inhibit this conversion) comprise a second class of protective agent for inclusion in the unit dose kit of the invention. A few compounds have been reported as potent inhibitors of adenosine kinase with $K_i$'s of less than 100 nM, including 5'-amino-5'-deoxyadenosine [Miller et al., *J. BioL Chem.*, 254: 2346–2352 (1979)]; 1,12-bis (adenosin-$N^6$-yl)dodecane [Prescott et al., *Nucleosides & Nucleotides*, 8: 297 (1989)]; 5-iodotubercidin [Henderson et al., *Cancer Chemotherapy Rep. Part* 2, 3: 71–85 (1972); Bontemps et a., *Proc. Natl. Acad. Sci. USA*, 80: 2829–2833 (1983); Davies el al., *Biochem. Pharmacol*, 35: 3021–3029 (1986)]; and 5'-deoxy-5-iodotubercidin [Davies et al. (1986)]. Brown et al., U.S. Pat. No. 5,864,033, reports nucleoside analog compounds that are purportedly potent and selective adenosine kinase inhibitors. The Brown patent also describes cell-free and cell-based in vitro assays for screening compounds for adenosine kinase inhibitory activity. Ugarkar et al., U.S. Pat. Nos. 5,795,977 and 5,763,597, report water soluble adenosine kinase inhibitors which are stated to be useful for treatment of cardiovascular and cerebrobvascular diseases, and which are contemplated as useful as a protective agent in this invention. All of the above-cited literature and patent documents are incorporated by reference. Any compound displaying adenosine kinase inhibitory activity at concentrations that display acceptable toxicity profiles are considered appropriate for use in the invention.

In a related embodiment, the protective agent comprises uridine, cytidine, and/or thymidine or their nucleosides. Such a protective agent is administered at a molar ratio of 1:1 to 1000:1 with the dose of adenosine, and more preferably 10:1 to 100:1.

In yet another embodiment, the protective agent comprises a compound that inhibits uptake of the ADAI or AMPDAI by cells.

As a related aspect, the invention provides the use of combinations of compounds or compositions as described above for the manufacture of a medicament for the treatment or neoplastic diseases. In a preferred embodiment, the manufacture of a medicament for the treatment of neoplastic diseases of cells of an epithelial origin are contemplated.

In a related embodiment, the invention provides methods of using the compositions and unit doses of the invention to kill neoplastic cells in vitro or in vivo. For example, the invention includes a method for inducing cell death in neoplastic cells, comprising: administering a composition according to the invention to a patient having neoplastic cells sensitive to the composition, in an amount sufficient to induce cell death in the neoplastic cells. The invention also includes a method for inducing cell death in neoplastic cells, comprising: administering a unit dose according to the invention to a patient having neoplastic cells sensitive to the compositions which comprise the unit dose, to induce cell death in the neoplastic cells. The administering is repeated as necessary and as tolerated by the patient in order to achieve the anti-neoplastic therapeutic benefit.

The invention also provides a method of treating a neoplastic disease state in a patient in need of such treatment, comprising the steps of: administering to a patient suffering from a neoplastic disease state a first compound selected from the group consisting of adenosine, adenosine derivatives, and pharmaceutically acceptable salts thereof, and a second compound selected from the group consisting of adenosine deaminase inhibitors (ADAI), adenosine monophosphate deaminase inhibitors (AMPDAI), and pharmaceutically acceptable salts thereof.

Although methods of the invention may be used to treat any neoplastic disease state, it is specifically contemplated that the methods be used to treat neoplastic diseases of cells, tissues, or organs of epithelial origin. Such epithelial malignancies include malignancies of the lungs, breasts, gastrointestinal system, genitourinary tract, or reproductive organs, many of which are considered refractory to many existing cancer therapies. In a highly preferred embodiment, the invention provides improved methods of treating ovarian cancer.

As explained above, the compounds are preferably formulated as compositions with one or more pharmaceutically acceptable carriers. They may be administered serially or simultaneously, and may be administered as part of a single formulation or as two separate formulations. Irrespective, a therapeutically effective amount of the compounds is administered to the patient. A therapeutically effective dose refers to that amount of the compounds that results in a reduction in the rate of growth of the undesired neoplastic cells, or more preferably a killing of the neoplastic cells resulting in their reduction or elimination to prolong the survival of the patient. The therapeutically effective dose also is a dose with acceptable levels of toxicity. In many cases a considerable level of toxicity or side effects is considered acceptable due to the lethality of the neoplastic disease state if left untreated.

Toxicity and therapeutic efficacy of such compounds can be determined by standard pharmaceutical procedures using, e.g., cell cultures and/or experimental animals. For example, one determines the $LD_{50}$ (the dose lethal to 50% of the population) and the $ED_{50}$ (the dose therapeutically effective in 50% of the population) in an accepted laboratory animal model to provide guidance for human dosing. The dose ratio between toxic and therapeutic effects is the therapeutic index and it can be expressed as the ratio $LD_{50}/ED_{50}$. Combinations of compounds which exhibit large therapeutic indices (preferably greater 2; more preferably greater than 10 or greater than 50) are preferred. The dosage required to achieve the desired concentration of therapeutic agents in the environment of a tumor will vary depending upon the dosage form employed and the route of administration utilized.

Cell culture assays and in vivo animal model studies, such as those described herein, permit initial estimates of therapeutically effective doses. Monitoring concentrations of the therapeutic compounds in the plasma, and/or in the tumor environment provide additional guidance.

The effective anti-cancer amount of the compounds are administered to patients in a manner that inhibits or prevents tumor growth and/or metastasis. In view of the teachings herein, the attending physician will be able to vary the amount of the compounds, the carrier, the dosing frequency, and the like, taking into consideration such factors as the particular neoplastic disease state and its severity; the overall condition of the patient; the patient's age, sex, and weight; the mode of administration; the suitability of concurrently administering systemic anti-toxicity agents; monitoring of the patient's vital organ functions; and other factors typically monitored during cancer chemotherapy.

Although an appropriate formulation, route of administration, dose, and dosing schedule, and duration of treatment can be optimized by a patient's physician according to the teachings herein, in preferred embodiments it is contemplated that the pharmaceutical formulations are administered to obtain concentrations of the compounds in the region of the tumor of about 0.01 to 1000 $\mu$M, and preferably about 0.5 to 500 $\mu$M, more preferably about 1 to 100 $\mu$M, and more preferably about 10 to 50 $\mu$M or about 20 $\mu$M. In a preferred embodiment, the molar ratio of the two compounds in the region of the tumor is 0.01 to 100; in a highly preferred embodiment 0.1 to 10; and in a very highly preferred embodiment, about 1.0.

As explained above, certain agents such as homocysteine compounds are expected to enhance the anti-tumor efficacy of the adenosine/enzyme inhibitor combination therapy of the invention. Methods of treatment that include administration of homocysteine compounds or other additional compounds to a patient, in amounts effective to increase the anti-neoplastic activity of the first and second compounds, are specifically contemplated.

The combination of therapeutic compounds may be administered by any route of drug administration, depending on the site of the cancer to be attacked. These include parenteral, intravenous, intracavitary, intrathecal, interstitial, intravesicular, intraperitoneal, topical, transdermal, transmucosal, and the like. Repeated injections or continuous infusions of the drug combination lasting for hours or days is contemplated, as toxicity permits, until the desired therapeutic results have been achieved. Continuous regional or system infusions by drug delivery pump is specifically contemplated.

In a highly preferred embodiment for treating many patients, especially patients wherein a cancer has not metastised, a route of administration is selected to maximize the concentration of the therapeutic agents in the region of the tumor while minimizing the systemic concentration, e.g., in the peripheral blood or plasma. For example, to treat a cancer localized to the peritoneal cavity, such as ovarian cancer, at least one of the first and second therapeutic compounds (and preferably both) is infused into the peritoneal cavity, e.g., with a catheter and/or a drug delivery pump, to effect a higher concentration of the agent in the peritoneal cavity than in the peripheral blood. The infusion is continued or repeated as necessary to maintain a desired therapeutic concentration of the chemotherapeutic compounds in the peritoneal cavity for, e.g., 12 to 24 hours.

In a related aspect, the invention provides for co-treatment of the patient with a protective agent, such as a nucleoside transport inhibitor or adenosine kinase inhibitor as described above, in an amount effective to reduce systemic toxic side-effects of the anti-neoplastic compounds. For example, a patient that is being given intraperitoneal injections or infusions for treatment of a localized tumor in the peritoneal cavity is simultaneously administered a pharmaceutical preparation of a protective agent intravascularly. The dosing of the protective agent is selected to achieve a systemic concentration that is high enough to prevent at least some of the toxic side effects of the anti-neoplastic agents, but is low enough so as not to significantly diminish the anti-neoplastic effects of the compounds on the tumor itself This balance is achievable by using routes of administration that induce higher concentrations of the anti-neoplastic agents in and around the tumor than in the patient as a whole, or in organs or fluids containing lymphoid cells particularly susceptible to toxic side effects. For example, the anti-neoplastic agents are administered locally to the tumor, to achieve high local concentrations thereof, while the protective agent is systemically administered at concentrations that are protective against the lower systemic concentrations of the anti-neoplastic agents, but not against the higher concentrations localized around the tumor. Alternatively, the protective agent itself is administered locally, to protect one or more healthy organs that would otherwise be particularly susceptible to the toxic side-effects of the neoplastic compounds. This concentration differential is maintained by periodically or continuously monitoring concentrations of the agents in the patient, and/or by knowledge of the pharmacokinetics of the different agents.

The invention is further described by reference to the following examples, which are intended as illustrative only and not as limiting the invention.

EXAMPLE 1

Anti-tumor Efficacy of Adenosine and Coformycin Combination Against Cultured Epithelial Cancer Cell Lines The following experimental protocols demonstrate that adenosine in combination with a deaminase inhibitor, namely coformycin, is an effective combination chemotherapy for killing two different cancer cell lines representing tumors of epithelial origin, namely breast and ovarian tumors.

For the experiments MCF7 breast cancer cells and OVCAR3 ovarian cancer cells (both obtained from the American Type Culture Collection (ATCC), Manassas, Va.) were cultured in RPMI 1640 media containing 10% fetal calf serum (Life Technologies, Gaithersburg, Md.). After 24 hours of culturing at 37° C. in 5% $CO_2$, additional medium was added containing either adenosine (final concentration 10 $\mu$M), coformycin (final concentration 10 $\mu$M), or 10 $\mu$M each of adenosine and coformycin. Additional media alone was added to control cultures.

The cells were cultured in these chemotherapeutic media for an additional 60 hours, at which time the viability of the cells were determined using an MTT assay (Celltitre 98 Aqueous 1, Promega, Madison, Wis.). FIG. 1 depicts the results of this assay, where cell viability as a percentage of control is depicted, with error bars to indicate standard deviation (representative of three different analyses). As can be seen in the figure, neither chemotherapeutic agent was effective alone at arresting cell growth, with cell viability measuring in excess of 100% of the controls. However, the combination chemotherapy was toxic to both tumor cell lines.

EXAMPLE 2

Figure 2:
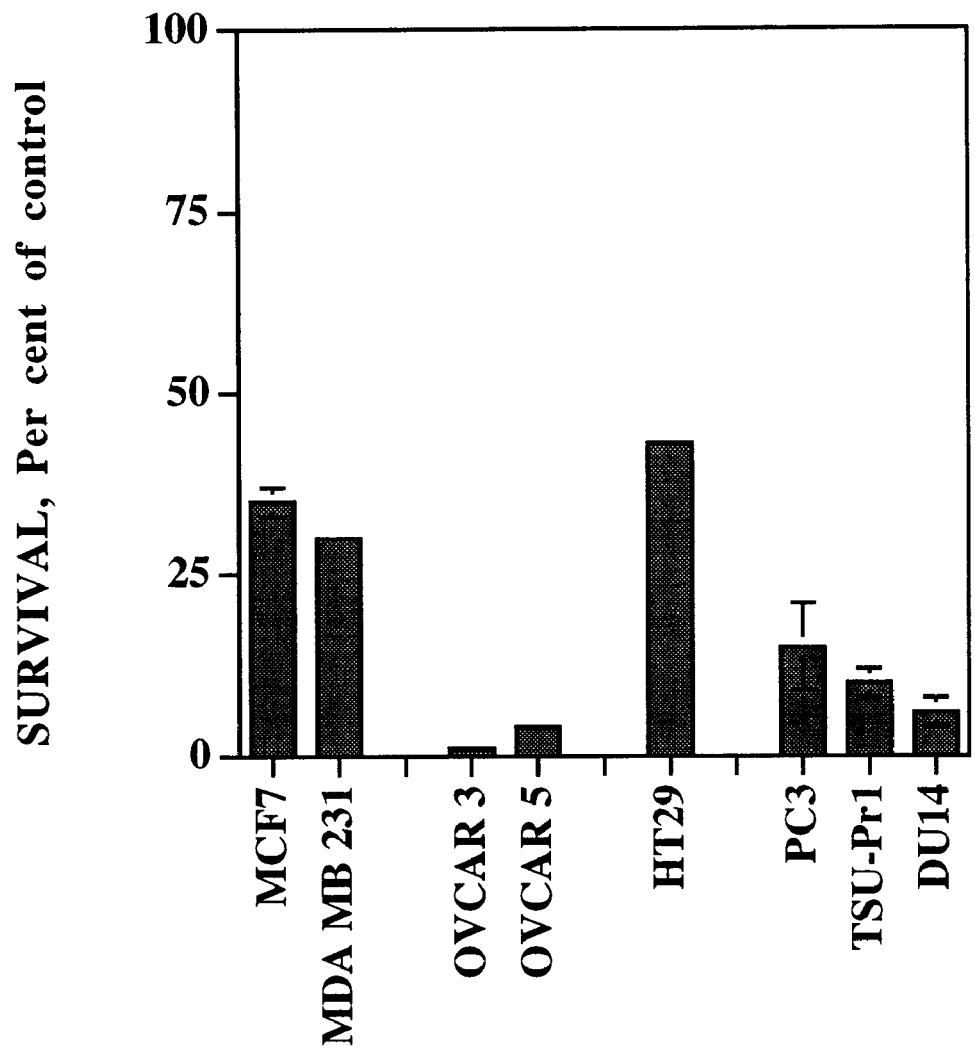
FIG. 2 is a bar graph depicting the efficacy of 10 $\mu$M adenosine combined with 10 $\mu$M coformycin for killing several tumor cell lines: MCF7 and MDA MB 231 breast cancer cell lines; OVCAR 3 and OVCAR 5 ovarian cancer cell lines; HT 29 colon cancer cell line; and PC3, TSU-Pr1, and DU14 prostatic cancer cell lines. The results are presented as the percent of surviving cells (compared to an untreated control) following a sixty hour exposure to the drug combination.

Anti-tumor Efficacy of Adenosine and Coformycin Combination Against Additional Cultured Epithelial Cancer Cell Lines The procedures described in Example I were repeated to test the anti-tumor efficacy of the adenosine/coformycin combination against several additional cell lines obtained from the ATCC: MCF7 and MDA MB 231 breast cancer cell lines; OVCAR 3 and OVCAR 5 ovarian cancer cell lines; HT 29 colon cancer cell line; and PC3, TSU-Pr1, and DU14 prostatic cancer cell lines. FIG. 2 depicts the results of this assay, where cell viability as a percentage of control is depicted, with error bars to indicate standard deviation (representative of three different analyses). As can be seen in the figure, the combination of 10 $\mu$M adenosine and 10 $\mu$M coformycin reduced survival of all tested tumor cell lines by at least 50%, and was highly effective against the prostatic and ovarian cancer cell lines.

EXAMPLE 3

Identification of Anti-toxicity Agents to Improve Safety and Prevent Systemic Oxicity In a preferred embodiment, patients that are treated with the chemotherapeutic combination of the invention to destroy localized tumors are additionally treated systemically with a drug designed to block the cellular uptake of at least one of the chemotherapeutic agents. As demonstrated in Example 1, blocking one agent is sufficient to reduce or eliminate toxicity. Systemic administration of a protective agent will prevent toxicity to non-cancerous tissues and also permit local administration of higher chemotherapeutic doses at the site of tumors.

Figure 3:
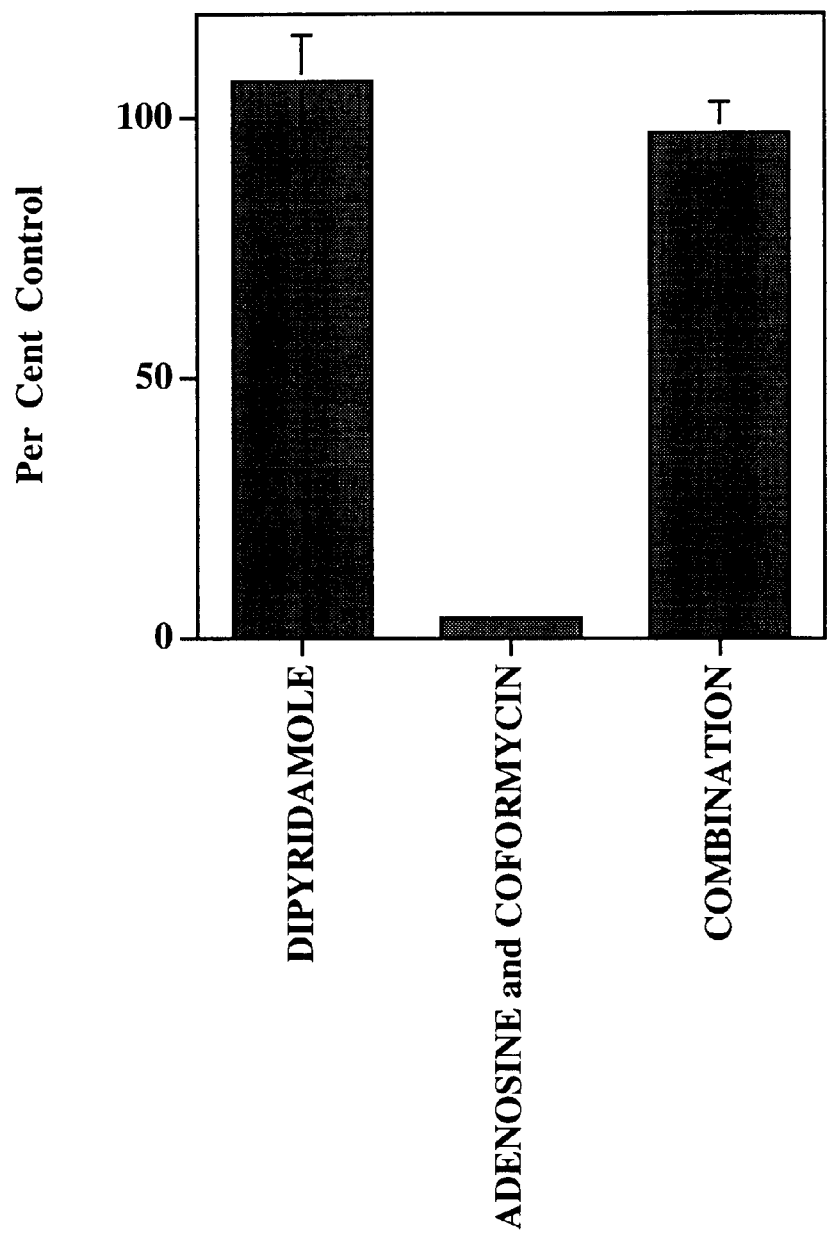
FIG. 3 is a bar graph depicting the efficacy of adenosine in combination with coformycin for killing cells of an ovarian cancer (OVCAR3) cell line, and the ability of the nucleoside transport inhibitor dipyridamole to protect the cells from the cytotoxic effects of this drug combination. The results are presented as the percent of viable (surviving) cells (compared to an untreated control) following a sixty hour treatment regimen.

Assays were performed to determine whether the nucleoside transport inhibitor dipyridamole or the adenosine kinase inhibitor 5'-amino-5'-deoxyadenosine were capable of protecting sensitive cell lines from the combination Ado/CF chemotherapy. The OVCAR3 ovarian cancer cell line was cultured as described in Example 1 for 24 hours and then treated with either 5 $\mu$M (final concentration) dipyridimole alone; 10 $\mu$M adenosine plus 10 $\mu$M coformycin alone; or the combination of these two treatments. In a control sample, culture media alone was added. The cultures were grown for an additional 60 hours and then analyzed for cell growth. The results of the assay are depicted in FIG. 3, where cell viability as a percentage of the control is depicted, with error bars to indicate standard deviation (representative of three different analyses). As shown therein, treatment with dipyridamole alone permitted cell growth comparable to the control, whereas the Ado/CF combination therapy reduced cell growth to less than 10% of the control. When dipyridamole was added in combination with the toxic levels of Ado/CF, the cancer cells again were able to grow at levels approximating that of the untreated control.

Figure 4:
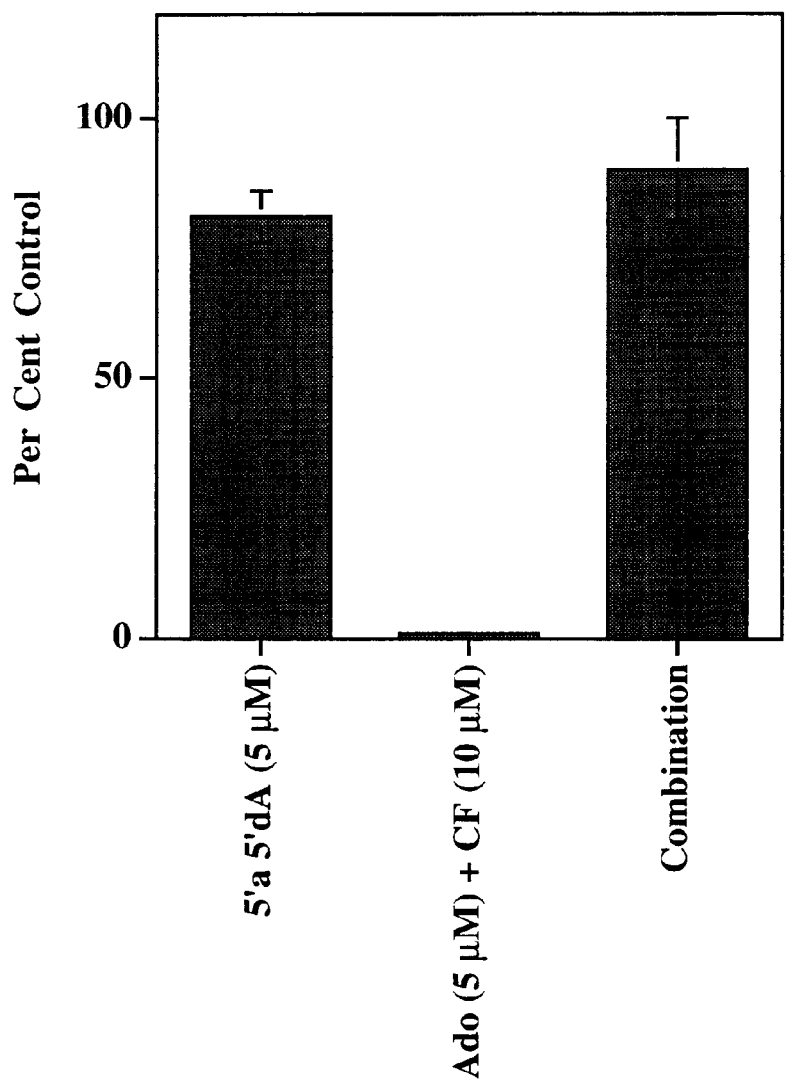
FIG. 4 is a bar graph depicting the efficacy of adenosine in combination with coformycin for killing cells of an ovarian cancer (OVCAR3) cell line, and the ability of the adenosine kinase inhibitor 5'-arnino-5'-deoxyadenosine to protect the cells from the cytotoxic effects of this drug combination. The results are presented as the percent of viable (surviving) cells (compared to an untreated control) following a sixty hour treatment regimen.

The same experiments were repeating using 5 $\mu$M (final concentration) 5'-amino-5'-deoxyadenosine alone; 5 $\mu$M adenosine plus 10 $\mu$M coformycin alone; or the combination of these two treatments. As depicted in FIG. 4, the 5'-amino-5'-deoxyadenosine was mildly toxic to the cancer cells when administered alone (cell growth ~80% of control), but was able to essentially completely block the severe toxic effects of the Ado/CF combination treatment.

Figure 5:
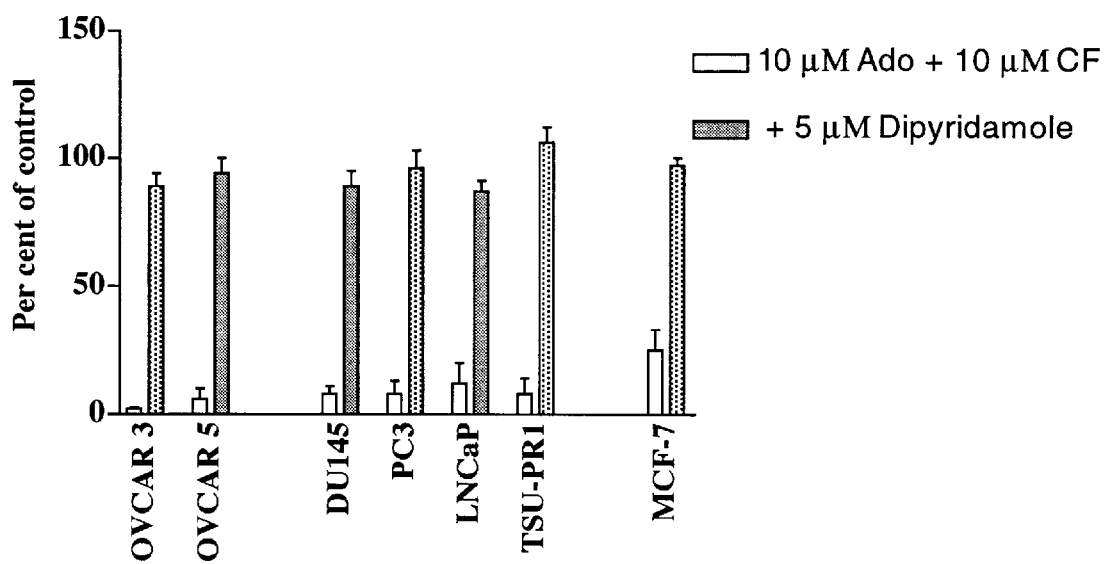
FIG. 5 is a bar graph depicting the efficacy of adenosine in combination with coformycin for killing cells of several cancer cell lines (OVCAR3, OVACAR5, DU145, PC3, LNCaP, TSU-PR1, and MCF-7), and the ability of the nucleoside transport inhibitor dipyridamole to protect the cells from the cytotoxic effects of this drug combination. The results are presented as the percent of viable (surviving) cells (compared to an untreated control) following a sixty hour treatment regimen. Error bars depict standard deviation (representative of three different analyses).

The dipyridimole experiment was repeated using several different tumor cell lines obtained from the ATCC: OVCAR3, OVCAR5, DU145, PC3, LNCaP, TSU-PR1, and MCF-7. As depicted in FIG. 5, the dipyridamole treatment consistently was able to protect the otherwise-sensitive tumor cell lines from the cytotoxic effects of Ado/CF treatment.

The foregoing data provides evidence that a nucleoside transport inhibitor and/or an adenosine kinase inhibitor are capable of protecting cells against the toxic effects of adenosine/coformycin combination therapy, and thus indicate a therapeutic use for such agents to protect healthy tissues during localized cancer chemotherapy.

EXAMPLE 4

Coformycin is More Potent than Deoxycoformycin when Used with Adenosine in Tumor Cell Toxicity Assays Existing literature recognizes both coformycin (CF) and deoxycoformycin (dCF) as inhibitors of adenosine deaminase (ADA) and AMP dearinase (AMPDA) enzymes. Whereas dCF is recognized as a more potent inhibitor of ADA than CF by 2.5-fold [$K_i$=0.01 nM versus 0.025 nM, see Cha S., et al., Biochem. Pharmacol 24: 2187–2197 (1975), and Agarwal, R P. et al., Biochem. Pharmacol 26: 359–367 (1977)], CF is a 50-fold more potent inhibitor of AMPDA. The following experiments were conducted to compare the anti-tumor efficacy of adenosine in combination with each of these dearninase inhibitors against a tumor cell line of epithelial origin.

Figure 6:
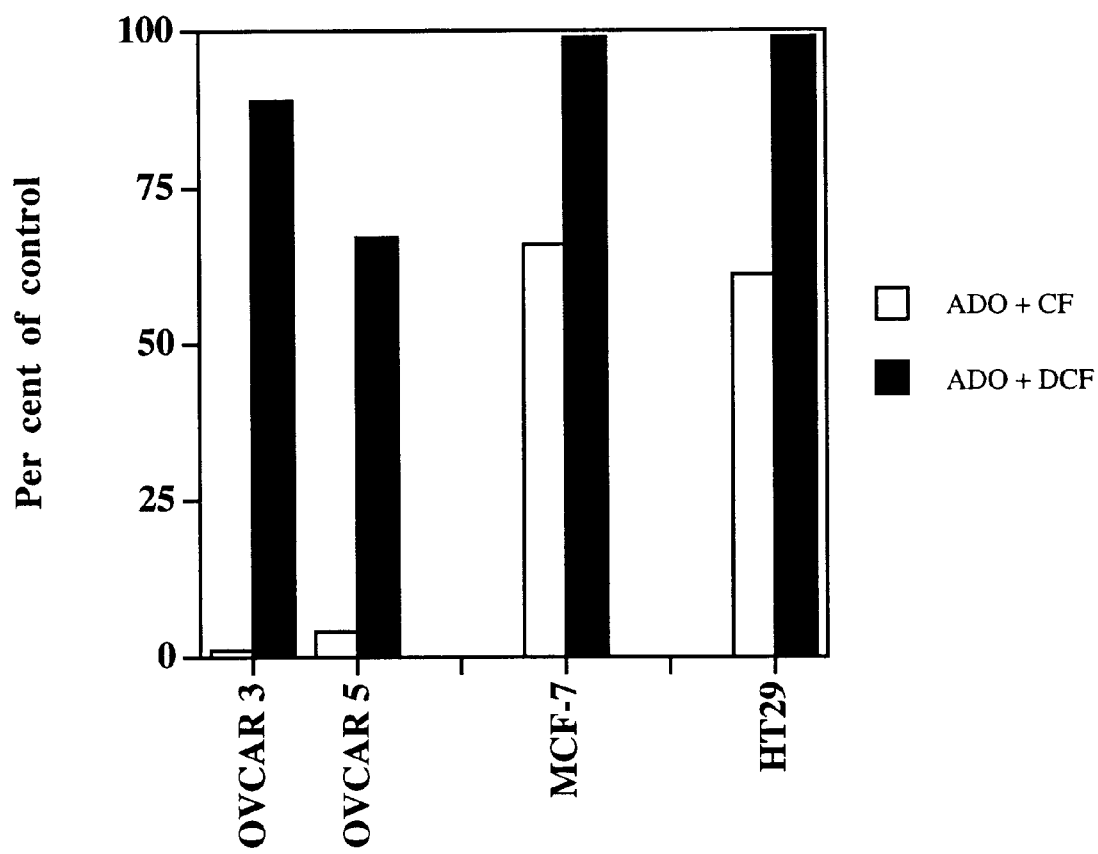
FIG. 6 is a bar graph depicting the efficacy of adenosine in combination with either coformycin or deoxycoformycin for killing cells of several cancer cell lines (OVCAR3, OVACAR5, MCF-7, HT29). The results are presented as the percent of viable (surviving) cells (compared to an untreated control) following a sixty hour treatment regimen.

The procedures described in Example 1 were repeated using cell lines OVCAR 3, OVCAR 5, MCF7, and HT 29 and using 5 $\mu$M adenosine in combination with either 5 $\mu$M CF or 5 $\mu$M dCF as the therapeutic combination of agents. FIG. 6 depicts the results of this assay, where cell viability as a percentage of control is depicted. As can be seen in the figure, the coformycin consistently potentiated to toxicity of the adenosine to a greater extent than the deoxycoformycin, and the differences were especially striking against the ovarian cancer cell lines OVCAR3 and OVCAR5.

Without intending to be limited to any particular theory, the foregoing data suggests that the combination chemotherapy of the invention acts through a mechanism involving inhibition of AMPDA or inhibition of both AMPDA and ADA. Based on these data, AMPDA inhibitors are postulated to comprise a preferred class of compounds for use in the invention, in combination with adenosine. A combination of ADA and AMPDA inhibitors, either embodied in a single compound such as CF or as a combination of an ADA inhibitor compound and an AMPDA inhibitor compound, are also a preferred class of compounds for use with adenosine in the invention. Repetition of the foregoing experiments with compounds that selectively inhibit ADA or selectively inhibit AMPDA, alone or in combination, will identify the most effective type of inhibitor or inhibitor combination for each particular tumor type.

EXAMPLE 5

Adenosine is More Potent than Select Adenosine Derivatives when Used with an ADAI/AMPDAI in Tumor Cell Toxicity Assays The following experiments were performed to compare the cytotoxicity of adenosine and selected adenosine derivatives when used in combination with an ADAI or AMPDI compound.

The procedures described in Example 1 were repeated using the OVCAR 3 ovarian cancer cell line, and using as therapeutic agents 10 $\mu$M coformycin in combination with 10 $\mu$M of either adenosine, 2-chloroadenosine, 8-chloroadenosine, or 8-chloro-cAMP. Cell viability data, determined as described above, is presented in the following table.

| Compound | Viability (Per Cent of Control) |
| --- | --- |
| Adenosine (10 $\mu$M) and Coformycin (10 $\mu$M) | 3 ± 0.2 |
| 2-chloroadenosine (10 $\mu$M) and Coformycin (10 $\mu$M) | 111 ± 5 |
| 8-chloroadenosine (10 $\mu$M) and Coformycin (10 $\mu$M) | 94 ± 6 |
| 8-chloro-cAMP (10 $\mu$M) and Coformycin (10 $\mu$M) | 98 ± 3 |

As can be seen from the table, the adenosine was a much more potent cytotoxic agent when used in combination with CF than any of the adenosine derivatives tested.

The foregoing results demonstrate that the use of adenosine in therapeutic combinations of the invention confers greater antineoplastic activity against at least certain cell types than a number of adenosine derivatives. In addition, use of adenosine provides the additional advantage that its toxic side-effects can be modulated using certain antitoxicity agents, as described above. Dipyridamole has shown to be ineffective for blocking the toxic effects of cordycepin when substituted for adenosine in experiments such as those described in Example 3.

EXAMPLE 6

In Vivo Anti-tumor Efficacy

Female nude mice (Harlan Labs) that are seven weeks old are weight matched and randomly divided into several groups. The animals are maintained on standard laboratory diets and drinking water. All animals are injected abdominally with anywhere from approximately 2 cells to 1 million cells from a human or murine ovarian cancer cell line.

Beginning one day after tumor injection, the different groups of mice are each treated with a pharmaceutical composition comprising either adenosine alone, coformycin alone, adenosine plus coformycin at varying concentrations, or comprising the pharmaceutical carrier alone (control). For some groups, the pharmaceutical composition further includes homocysteine thiolactone. In one variation, intraperitoneal injections of the are performed at regular weekly intervals for eight weeks. In a preferred variation, after the initial injection into the peritoneal cavity, a drug delivery pump is used to continuously deliver selected amounts of the pharmaceutical compositions to the animals for, e.g., 12, 18, 24, 36, or 48 hours. Blood may be drawn from the ear or tails of animals to determine drug concentrations.

After 21–35 days of treatment, the animals are studied to determine treatment efficacy. Animal weight and duration of animal survival; measurements of tumor weight (following animal sacrifice), and/or other conventional factors are analyzed. Improved survival times and/or decreased tumor burden in the combination therapy groups compared to the control group and/or to the groups receiving single agents is considered indicative of therapeutic efficacy.

The experiment is repeated using alternative tumor cell lines; and/or using adenosine derivatives; and/or using alternative deaminase inhibitors to demonstrate therapeutic efficacy in other variations of the invention. The experiment is further repeated in alternative animal models, including models known to spontaneously develop various epithelial cancers and in larger mammals such as dogs, pigs, or primates, that more closely approximate humans.

EXAMPLE 7

Use of Anti-toxicity Agents In Vivo to Improve Safety and Prevent Systemic Toxicity Procedures described in Example 6 are repeated with the following variation. In addition to localized infusion of therapeutic agents into the peritoneal cavity, some animals are also injected intravenously, intraarterially, or intramuscularly with a pharmaceutical composition comprising selected concentrations of a protective agent such as a nucleoside uptake inhibitor or an adenosine deaminase inhibitor. Some animals receiving the protective agent are administered dosages of the therapeutic agents that are equivalent to or greater than the maximum doses tolerated in the studies wherein no protective agents were employed.

After 21–35 days of treatment, the animals are studied to determine treatment efficacy. Animal weight and duration of animal survival; measurements of tumor weight (following animal sacrifice), and/or other conventional factors are analyzed. Improved survival times and/or decreased tumor burden in the combination therapy groups that receive the protective agent, compared to groups that do not, is considered indicative of therapeutic efficacy. Therapeutic efficacy also is demonstrated by equivalent survival time combined with observed decreases in toxic side effects (e.g., fever, chills, diarrhea, loss of weight or appetite, etc.) in the animals that receive the protective agent.

While the present invention has been described in terms of specific embodiments, it is understood that variations and modifications will occur to those in the art, all of which are intended as aspects of the present invention. Accordingly, only such limitations as appear in the claims should be placed on the invention.

What is claimed is:

1. A method for potentiating cell death in neoplastic cells of epithelial origin, comprising: administering to a patient having neoplastic cells of epithelial origin:
   a first composition comprising adenosine or pharmaceutically acceptable salts thereof, and
   a second composition comprising a member selected from the group consisting of adenosine deaminase inhibitors (ADAI), adenosine monophosphate deaminase inhibitors (AMPDAI), and pharmaceutically acceptable salts thereof,
   wherein said compositions are adminstered in amounts effective to potentiate the death of neoplastic cells of epithelial region.

2. The method according to claim 1, wherein the fist composition comprises adenosine.

3. The method according to claim 2 wherein the second composition comprises a compound that is both an ADAI and an AWPDAI, or a pharmaceutically acceptable salt thereof.

4. The method according to claim 2 wherein the second composition comprises a compound that is an ADAI and a compound that is an AMPDAI.

5. The method according to claim 2 wherein the first and second compositions are in admixture and further include a pharmaceutically acceptable carrier.

6. The method according to claim 2 further including a composition that comprises homocysteine in an amount effective to potentiate the anti-neoplastic activity of the first and second compositions.

7. The method according to claim 2 wherein the first and second compositions are not in admixture.

8. A method for inducing cell death in neoplastic cells of epithelial origin, comprising: administerig a composition to a patient having neoplastic cells of epithelial origin sensitive to said composition, in an amount sufficient to potentiate cell death in said neoplastic cells, wherein the composition comprises:
   a first compound that is adenosine, in admixture with a second compound selected from the group consisting of adenosine deaminase inhibitors (ADAI), adenosine monophosphate deaminase inhibitors (AMPDAI), and pharmaceutically acceptable salts thereof, and
   a pharmaceutically acceptable carrier.

9. A method of treating an epithelial malignancy in a patient in need of such treatment, comprising the steps of:
   identifying or selecting a patient suffering from an epithelial malignancy,
   administering to the patient a combination of a first compound comprising adenosine or pharmaceutically acceptable salts thereof, and
   a second compound selected from the group consisting of adenosine deaminase inhibitors (ADAI), adenosine monophosphate deaminase inhibitors (AMPDAI), and pharmaceutically acceptable salts thereof, wherein said first and second compounds are present in said combination in amounts effective to potentiate treatment of said epithelial malignancy.

10. The method according to claim 9 wherein the second compound has both ADAI and AMPDAI activity.

11. The method according to claim 9 wherein the second compound is an ADAI or phannaceutically acceptable salt thereof, and wherein the method further comprises the step of administering to the patient an AMPDAI or pharmaceutically acceptable salt thereof.

12. The method according to claim 9 wherein the first and second compounds are administered simultaneously in a pharmaceutically acceptable carrier.

13. The method according to claim 9 wherein the epithelial malignancy is selected from malignancies of the lungs, breasts, gastrointestinal system, genitourary tract, or reproductive organs.

14. The method according to claim 9 wherein the epithelial malignancy is ovarian cancer.

15. The method according to claim 9 wherein the administering of at least one of said first and second compounds is performed to effect a higher concentration thereof in or around said tumor than in the peripheral blood.

16. The method according to claim 15 wherein the malignancy is situated in the peritoneal cavity, and wherein the administering step comprises infusing the compositions into the peritoneal cavity.

17. The method according to claim 16 wherein the infusing is performed through a catheter inserted into the peritoneal cavity.

18. The method according to claim 17 wherein the infusing is continued to maintain a peritoneal concentration of the compounds of at least 5 $\mu$M for at least 12 hours.

19. The method according to claim 17 wherein the infusing is continued to maintain a peritoneal concentration of the compounds of about 5 $\mu$M–20 $\mu$M for at least 12 hours.

20. The method according to any one of claims 9, 10, 12, 13 or 14, wherein the second compound is coformycin in an amount effective to potentiate treatment of said epithelial malignancy.

21. The method according to claim 20 wherein a composition comprising the coformycin is administered to generate a higher concentration of coformycin localized to neoplastic cells and lower systemic concentrations of coformycin.

* * * * *

UNITED STATES PATENT AND TRADEMARK OFFICE
CERTIFICATE OF CORRECTION

PATENT NO. : 6,579,857 B1
DATED : June 17, 2003
INVENTOR(S) : Stuart E. Lind et al.

It is certified that error appears in the above-identified patent and that said Letters Patent is hereby corrected as shown below:

Column 2,
Line 40, replace "3'-deoxadenosine" with -- 3'- deoxyadenosine --.

Column 3,
Line 25, replace "3 -deaxaadenosine" with -- 3-deazaadenosine --.

Column 5,
Line 55, replace "thereof" with -- thereof. --.

Column 6,
Line 44, replace "DU14" with -- DU145 --.
Line 59, replace "5'-arnino-5'-deoxyadenosine" with -- 5'-amino-5'-deoxyadenosine --.
Line 66, replace "OVACAR5" with -- OVCAR5 --.

Column 7,
Line 10, replace "OVACAR5" with -- OVCAR5 --.
Line 22, replace "thereof" with -- thereof. --.
Line 63, replace "10 $\mu$M" (second occurrence) with -- 10 mM --.

Column 8,
Line 10, replace "dearinase" with -- deaminase --.
Line 22, replace the space between "5,731,432 ," and "5,731,432,".
Line 50, replace "caraboxylmethyl" with -- carboxylmethyl --.
Line 53, replace "sorbit" with -- sorbitan --.

Column 9,
Line 63, replace "is" with -- are --.

Column 10,
Line 10, replace "dipyridimole" with -- dipyridamole --.
Line 39, replace "cerebrobvascular" with -- cerebrovascular --.
Line 57, replace "or" with -- of --.

Column 11,
Line 1, replace "inducingcell" with -- inducing cell --.
Line 54, replace "greater 2" with -- greater than 2 --.

Column 12,
Line 40, replace "system" with -- systemic --.
Line 44, replace "metastised" with -- metastasized --.

UNITED STATES PATENT AND TRADEMARK OFFICE
CERTIFICATE OF CORRECTION

PATENT NO.     : 6,579,857 B1
DATED          : June 17, 2003
INVENTOR(S)    : Stuart E. Lind et al.

It is certified that error appears in the above-identified patent and that said Letters Patent is hereby corrected as shown below:

Column 13,
Line 3, replace "itself," with -- itself. --.
Line 50, replace "Celltitre 98" with -- Celltiter 96 --.

Column 14,
Line 4, replace "DU14" with -- DU145 --.
Lines 5 and 11, replace "prostatic" with -- prostate --.
Line 17, replace "Oxicity" with -- Toxicity --.

Column 15,
Lines 13 and 21, replace "dearinase" with -- deaminase --.
Line 29, delete "to".

Column 16,
Line 19, replace "has" with -- has been --.
Line 39, replace "the" with -- the compounds --.
Line 48, replace ";" with -- , --.

Column 17,
Line 12, replace ";" with -- , --.
Line 43, replace "fist" with -- first --.
Line 47, replace "AWPDAI" with -- AMPDAI --.
Line 62, replace "administerig" with -- administering --.

Column 18,
Line 26, replace "phannaceutically" with -- pharmaceutically --.
Line 35, replace "genitourary" with -- genitourinary --.

Signed and Sealed this

Twenty-fifth Day of November, 2003

JAMES E. ROGAN
*Director of the United States Patent and Trademark Office*